United States Patent [19]

Philippe et al.

[11] Patent Number: 5,045,533
[45] Date of Patent: Sep. 3, 1991

[54] RETINOIC ESTERS OF ANTIBIOTICS AND PHARMACEUTICAL AND COSMETIC COMPOSITIONS CONTAINING THEM

[75] Inventors: Michel Philippe, Antony; Henri Sebag, Paris; Didier Dupuis, Le Raincy; André Rougier, Dammartin en Goele, all of France

[73] Assignee: L'Oreal, Paris, France

[21] Appl. No.: 235,853

[22] Filed: Aug. 24, 1988

Related U.S. Application Data

[63] Continuation-in-part of Ser. No. 46,017, May 5, 1987, abandoned.

[30] Foreign Application Priority Data

May 6, 1986 [FR] France .................................. 86 06528
Nov. 4, 1987 [LU] Luxembourg ........................... 87041

[51] Int. Cl.$^5$ ...................... A61K 31/70; C07H 17/08; C07H 15/16
[52] U.S. Cl. .......................................... 514/29; 514/24; 514/30; 514/844; 514/859; 536/7.1; 536/7.2; 536/16.2
[58] Field of Search ......................... 536/7.1, 7.2, 16.2; 514/24, 29, 30, 844, 859

[56] References Cited

U.S. PATENT DOCUMENTS 4,575,497 3/1986 Omura et al. ......................... 536/7.1

Primary Examiner—Elli Peselev
Attorney, Agent, or Firm—Cushman, Darby & Cushman

[57] ABSTRACT

All trans or 13-cis retinoic acid esters of macrolide and lincosamide antibiotics. These esters are useful in the therapeutic and cosmetic treatment of dermatosis and principally in the treatment of acne.

12 Claims, No Drawings

RETINOIC ESTERS OF ANTIBIOTICS AND PHARMACEUTICAL AND COSMETIC COMPOSITIONS CONTAINING THEM

This application is a continuation-in-part of application, Ser. No. 07/046,017, filed May 5, 1987, now abandoned.

The present invention relates to new retinoic esters of macrolide and lincosamide antibiotics. The present invention also relates to a process for the preparation of said esters and to pharmaceutical and cosmetic compositions containing them for the treatment of various dermatoses and principally for the treatment of acne.

Moreover, current studies also show that these retinoic esters according to the present invention exhibit anti-tumoral activity.

The present invention relates especially to the use of these new retinoic esters of antibiotics in the treatment of infectious or noninfectious dermatoses whose origin can be bacterial, mycobacterial and/or linked to the implantation of certain yeasts having a pathogenic characteristic.

The present invention envisages, more particularly, the use of these new retinoic esters of antibiotics in the treatment of acne.

Acne is a cutaneous disorder, polymorph, (several types of lesions existing on the body of an individual person) which occurs during puberty and regresses, in the majority of cases, at about the age of 20–25.

Acne concerns, in the affected individual, areas which are rich in sebaceous glands, such as the forehead, face, nose, torso and the back, thus evidencing that acne exhibits a certain dependence on sebum, which is a synthesis product of the gland.

Acne does not exist in the absence of seborrhea.

Although seborrhea in one expression of the sudden hormonal flow occurring at puberty, acne does not appear to be linked to any hormonal disorder.

The etiopathogency of acne, although poorly defined has its origin in the formulation of a characteristic lesion, the comedon. This results from the obstruction of the pilosebaceous canal, as a result of diskeratinization of the infundibilum zone of the duct.

This obstruction has, for a major effect, the modification of the sebum viscosity and the physico-chemical characteristics of the medium (pH, oxygen vapor pressure).

This modification permits hyperproliferation of cutaneous dwelling strains and, principally, *propionibacterium acnes*, anaerobic or aero-tolerant strain.

Acne has no infectious characteristics in the sense where this form of dermatosis does not correspond to the implantation of a particular pathogenic strain and it is not transmissible.

Finally, the bacterial hyperproliferation results in the liberation, in certain medium, of proteases or hyaluronidases, of bacterial origin, which provokes a lysis of the follicular sac and thus releases inflammatory compounds in the derm thereby causing an inflammatory type reaction of the organism.

If the nature of the inflammatory compounds is, at present, not determined, their bacterial origin seems to be of little doubt, thereby explaining the good therapeutic success achieved in inflammatory acne, using antibiotic products, both orally and topically.

Among antibiotics erythromycin and clindamycin are quite often recommended but the use of these particular antibiotics requires (principally for erythromycin) a relatively high concentration in order to obtain satisfactory results.

Moreover, as recent studies have shown, certain strains of *propionibacterium acnes* exhibit a progressive resistance to some antibiotics such that the treatment by these antibiotics have proven to be only slightly effective.

The topical application of antibiotics also runs into a problem of penetration through the corneum stratum thereby limiting their effectiveness.

The new retinoic esters of antibiotics, in accordance with the present invention, provide a satisfactory solution to the problems encountered by the use of antibiotics, in the measure where the studies carried out have evidenced that these new esters have a selective action of the principal germ responsible for the inflammation, i.e. *propionibacterium acnes*, all while having a very weak activity vis-à-vis cutaneous germs, such as *staphylococcus epidermidis* which permits the treatment of skin disorders without disturbing its equilibrium.

Moreover, these new retinoic esters of antibiotics, principally, the all trans and 13-cis retinoic esters have proven to be active vis-à-vis strains of *propionibacterium acnes* which are resistant to the parent antibiotic.

The new retinoic esters of antibiotics in accordance with the present invention have also proved to be active without exhibiting the disadvantages of retinoic acid.

Thus, these new esters are better tolerated by the skin and have proved to be much less toxic taken orally than is the combination of antibiotic/retinoic acid.

The retinoic esters of antibiotics according to the present invention, relative to other known esters of antibiotics, exhibit the advantage of possessing keratolytic activity in the case of esters of all trans retinoic acid and a potential anti-seborrhea activity in the case of 13-cis retinoic acid, which imparts to these esters a "prodrug" image.

The new retinoic esters of antibiotics, according to the present invention, are more lipophilic thereby improving penetration through the epidermis.

The state of the art relative to the esters of macrolide antibiotics is represented by U.S. Pat. No. 2,862,921 which relates to the preparation of mono-unsaturated and saturated fatty esters of erythromycin A, such as the monostearate of erythromycin A and the monooleate of erythromycin A.

The state of the art relative to the esters of lincosamide antibiotics is represented principally by German patent 2,017,003, which describes the preparation of esters of lincomycin and clindamycin whose acyl chain has from 1 to 18 carbon atoms.

The present invention relates to retinoic esters of macrolide and lincosamide antibiotics and more particularly to all trans and 13-cis esters of retinoic acid of such antibiotics and to the salts of said esters.

The retinoic esters of macrolide and lincosamide antibiotics according to the present invention can be represented by the following formula:

$$\text{(I)}$$

wherein:

R represents a macrolide or lincosamide residue, and mixtures and salts of said esters.

Among the macrolides, it can be mentioned erythromycin A, roxithromycin, oleandomycin, josamycin and the spiramycins (I), (II) and (III).

Among the lincosamides it can be mentioned lincomycin and clindamycin.

The retinoic esters of erythromycin A and roxithromycin can be represented by the following formula:

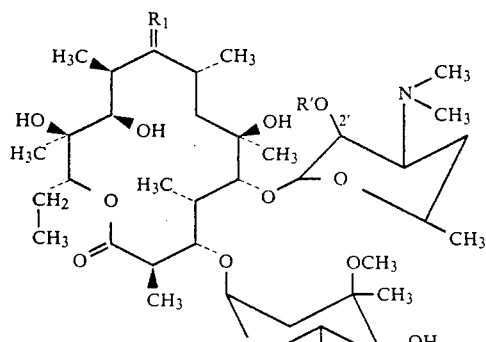

wherein:

R₁ represents O (erythromycin A) or N~O-CH₂-O-CH₂-CH₂-O-CH₃ (roxithromycin), and R' represents the acyl radical having the formula:

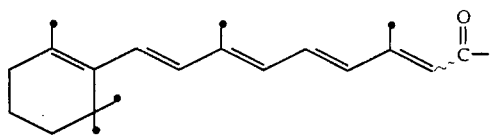

These retinoic esters of erythromycin A and roxyithromycin are those in the 2'-position.

The retinoic esters of oleandomycin can be represented by the following formula:

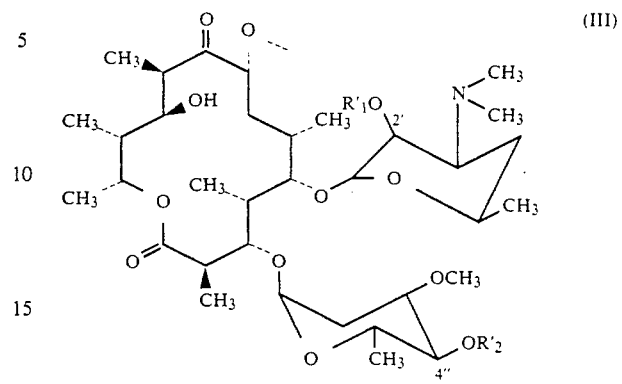

wherein:

R'₁ or R'₂ represents R' or an hydrogen atom with the proviso that at least one represents R', R' having the same meaning given above.

These retinoic esters of oleandomycin are those in the 2'- and/or 4"-position but they can be present in the form of a mixture.

The retinoic esters of josamycin can be represented by the following formula:

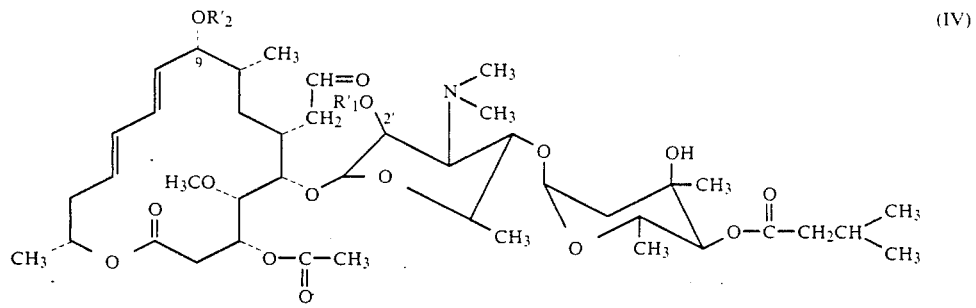

wherein: R'₁ or R'₂ represents R' or an hydrogen atom with the proviso that at least one represents R', R' having the same meaning given above.

These retinoic esters of josamycin are those in the 9- and/or 2'-position but they can be present in the form of a mixture.

The retinoic esters of spiramycins can be represented by the following formula:

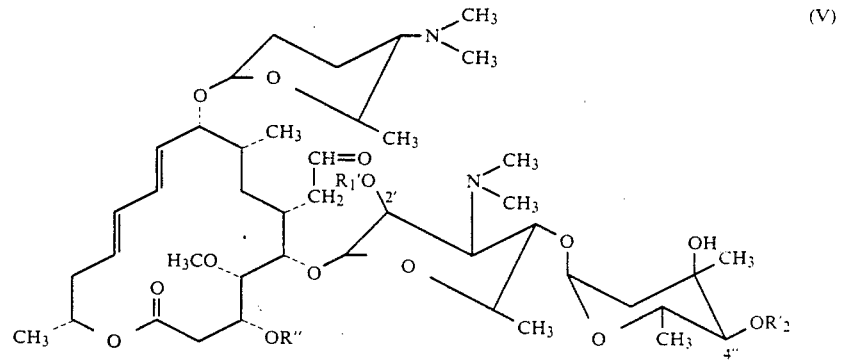

wherein:

R'₁ or R'₂ represents R' or a hydrogen atom with the proviso that at least one represents R', R' has the same meaning given above, and R" represents an hydrogen atom (spiramycin I), an acetyl radical (spiramycin II) or a propionyl radical (spiramycin III).

These esters of spiramycins (I), (II) and (III) are those in the 2'- and/or 4"-position but they can be present in the form of a mixture.

The retinoic esters of lincomycin and clindamycin can be represented by the following formulas:

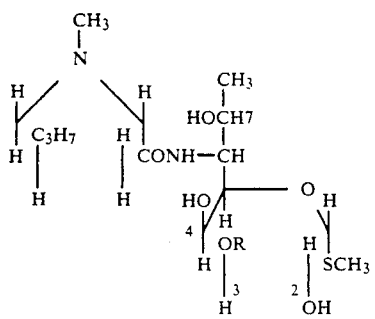
VI

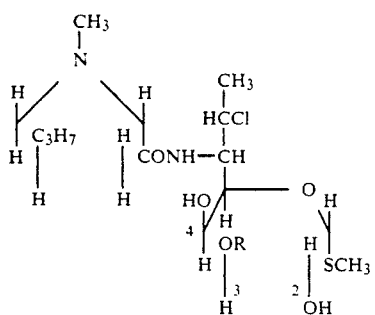
VII wherein: R' has the same meaning given above.

The esters of lincomycin (VI) and clindamycin (VII) are preferably in the 3-position. However they can be present in the form of mixtures with the lincomycin esters in the 2-, 4- and 7-positions and clindamycin esters in the 2-, and 4-positions.

The retinoic esters of formula (I) according to the invention are preferably selected form the group consisting of:
O-retinoyl (all trans)-2'-erythromycin A,
O-retinoyl (13-cis)-2'-erythromycin A,
O-retinoyl (13-cis)-2'-roxithromycin
O-retinoyl (all trans)-2'-oleandomycin
O-retinoyl (all-trans)-4"-josamycin
O-retinoyl (all trans)-9-josamycin
O-retinoyl (all trans)-2'-josamycin
O-retinoyl (13-cis)-2'-spiramycin (I), (II) and (III),
O-retinoyl (all trans)-3-spiramycin (I), (II) and (III),
O-retinoyl (13-cis)-9-josamycin,
O-retinoyl (13-cis)-3-lincomycin,
O-retinoyl (13-cis)-3-clindamycin,
O-retinoyl (all trans)-7-lincomycin,
O-retinoyl (all trans)-3-lincomycin,
O-retinoyl (all trans)-2-lincomycin,
O-retinoyl (all trans)-2-clindamycin,
O-retinoyl (all trans)-3-clindamycin,
O-retinoyl (all trans)-4-clindamycin.

The present invention also relates to a process for preparing the all trans and 13-cis retinoic esters of antibiotics according to the formula (I) above.

Various esterification procedures can be employed but, preferably, this esterification is carried out in an anhydrous organic solvent medium, preferably in tetrahydrofuran alone or in admixture with another organic solvent such as pyridine, by reacting an excess of mixed anhydride of all trans of 13-cis retinoic acids (prepared in situ, for example starting with ethyl chloroformate and all trans or 13-cis acid) with a macrolide or lincosamide such as mentioned above, in base form, in the presence of an organic or mineral base, such as pyridine and/or sodium bicarbonate and/or triethylamine.

This method, using the mixed anhydride, provides retinoic esters in the positions defined above in good yield conditions.

Other esterification procedures, principally of lincomycin and clindamycin, using retinoic acid imidazolides in an anhydrous solvent, such as N,N-dimethylformamide, in the presence of a base such as sodium or potassium tert butylate, lead to mixtures of retinoic esters of these antibiotics.

Thus by this latter method, the ester in the 7-position of lincomycin is predominately obtained with esters in the 2-, 3- and 4-positions.

Also a mixture of monoesters in the 2-, 3- and 4-positions of clindamycin is obtained.

The present invention also relates to pharmaceutical compositions which can be administered topically, orally, parenterally or rectally as well as to compositions having a cosmetic character for the treatment of various dermatoses, principally acne, this composition being provided in anhydrous form and containing at least one all trans or 13-cis retinoic acid ester of antibiotics according to the present invention, at a concentration between 0.001 and 10 percent but preferably between 0.01 and 1 percent, by weight, based on the total weight of the composition.

For the preparation of the compositions in accordance with the present invention containing, as the active component, at least one all trans or 13-cis retinoic ester of antibiotics, there can be employed those vehicles and adjuvants which are described in the literature directed to pharmacy, cosmetics and related fields.

For the preparation of solutions, there can be employed, for example, one or more organic solvents acceptable from a physiologic viewpoint.

The acceptable organic solvents are selected principally from the group consisting of acetone, isopropyl alcohol, triglycerides of fatty acids, $C_1-C_4$ alkyl esters of short chain acids, the ethers of polytetrahydrofuran and volatile silicones such as the cyclomethicones.

The compositions according to the present invention can also contain thickening agents, such as cellulose and/or cellulose derivatives, in an amount ranging from 0.5 to 20 percent by weight based on the total weight of the composition.

The compositions according to the present invention can also contain in combination, with at least one retinoic ester of antibiotics, according to the invention, at least one other known anti-acne agent.

If necessary, a conventional adjuvant selected from the group consisting of antioxidants, preservatives, perfumes and dyes can be included in the compositions of the present invention.

Representative useful antioxidants include, for example, tert.butyl hydroxyquinone, butyl hydroxyanisole, butylhydroxytoluene and α-tocopherol and their derivatives.

The pharmacologic and galenic transformations of the compounds, in accordance with the present invention, are carried out in a known manner.

The galenic forms can be for topical application to the skin and include creams, milk, gels, more or less thick lotions, pads impregnated with lotions, ointments, sticks or even aerosol formulations provided in the form of a spray or foam.

The compositions for oral administration can be provided in the form of tablets, gelules, lozenges, syrups, suspensions, emulsions, powders, granules or suspensions.

The posology by oral administration is about 0.1 mg to 5 mg/Kg of body weight/day and preferably about 1 mg to 2.5 mg/Kg/day.

The compositions can also be provided in the form of suppositories.

The treatment of acne with the topical compositions according to the present invention comprises applying two or three times each day a sufficient amount on the areas of the skin to be treated and this for a period of time ranging from 6 to 30 weeks and preferably from 12 to 24 weeks.

The compositions according to the present invention can also be used as a preventive, i.e. on the areas of the skin susceptible of being attacked with acne.

COMPARATIVE STUDY OF THE ACTIVITY OF RETINOIC ESTERS OF ANTIBIOTICS

The activity of retinoic esters of antibiotics namely of erythromycin A, lincomycin and clindamycin has been studied by the dilution method, so as to determine, the minimal inhibitory concentration (MIC), this method being described and employed by G. A. Denys et al, "Antimicrobial Agents and Chemotherapy" 1983) 23, 335–337 and J. J. Leyden et al, J. Am. Acad. Dermatol. (1983), 8, (1) 41–5, by using as the strain of *propionibacterium acnes*, the P37 strain furnished by Cunliffe and Holland.

This P37 strain is the object of studies described in the following publications:

J. Greenman, K. T. Holland and W. J. Cunliffe, Journal of General Microbiology (1983) 129, 1301–1307, E. Ingham, K. T. Holland, G. Gowland and W. J. Cunliffe, ibid (1980) 118, 59–65 and K. T. Holland, J. Greenman and W. J. Cunliffe, Journal of Applied Bacteriology (1979) 47 383–394.

SELECTION AND ISOLATION OF SENSITIVE AND RESISTANT POPULATIONS

The P37 strain is sensitive to erythromycin as shown by the minimal inhibitory concentration (MIC=0.78 $\mu$g/ml).

On the other hand, after 8 successive sub-cultures in the same medium (RCM, Reinforced Clostridium Medium (oxoid) 19/20, DMSO 10/20 by volume) so as to obtain a progressive stabilization of the strain to this medium, a progressive resistance to erythromycin is manifested in the following form.

After exposure of a standardized inoculum (DO=1.8 to 450 mm) on gelose medium (RCM+ furazolidone) in a Petri dish, a 9 mm diameter disk is deposited at its center. On this disk, 50 $\mu$g of erythromycin (in solution in DMSO) are deposited.

After 6 days at 36° C. in an anaerobic medium (GAS-PAK system, B. B. L) a zone of inhibition of the growth of the strain is clearly visible (total diameter=42 mm), the vast majority of the colonies being situated at the periphery of the zone of inhibition.

On the other hand at its interior a few colonies clearly appear.

The two types of colonies are retained by stripping off from the gelose medium (sterilized platinum loop):

(1) at the interior of the zone of inhibition strains called P37 E⊖ are retained because of their apparent resistance to erythromycin;

(2) at 1 cm beyond the periphery of the zone of inhibition strains called P37 E⊕ are retained.

After isolation and culture, the P37 E⊕ and P37 E⊖ strains effectively show very different sensitivities to erythromycin as is illustrated by the following respective MIC values:

|  | MIC ($\mu$g/ml) |
|---|---|
| P37 | 0.78 |
| P37 E⊕ | 0.78 |
| P37 E⊖ | 50 |

This phenomeon is confirmed by the study of the IC 50 (Inhibitory Concentration at 50%) which represents the concentration of erythromycin where, at a constant culture time, 50% of survivors among the population are found.

|  | IC 50 ($\mu$g/ml) |
|---|---|
| P37 | 50 |
| P37 E⊕ | 5 |
| P37 E⊖ | 100 |

The Minimal Inhibitory Concentration (MIC) expressed in $\mu$g/ml of the tested retinoic esters of erythromycin A, lincomycin and clindamycin vis-a-vis the P37⊕ and P37⊖ strains is reported in the following tables

|  | P37 E⊕ (sensitive) | P37 E⊖ (resistant) |
|---|---|---|
| Retinoic Esters of Antibiotics |  |  |
| O-retinoyl (all trans)-2'-erythromycin A | 14 | 13 |
| O-retinoyl (13-cis)-2'-erythromycin A | 20 | 34 |
| O-retinoyl (13-cis)-3-lincomycin | 17.5 | 25 |
| O-retinoyl (all-trans)-3-clindamycin | 18 | 50 |
| O-retinoyl (13-cis)-3-clindamycin | 1.5 | 35 |
| Controls |  |  |
| O-oleoyl-2'-erythromycin A (Z-9) | 50 | 100 |
| O-oleoyl-3-lincomycin | 19 | 42 |
| O-oleoyl-3-clindomycin | 54 | >138 |
| Erythromycin A | 1 | >50 |
| Lincomycin | 13 | 66 |
| Clindamycin | 1 | 10 |

The table below shows the minimal inhibitory concentrations of the retinoic esters of antibiotics vis-a-vis the two strains of *Staphylococcus Epidermidis*:

|  | Staph. Epi. 3 | Staph. Epi. 6 |
|---|---|---|
| Retinoic Esters of Antibiotics |  |  |
| O-retinoyl (all trans)-2'-erythromycin A | 75 | 80 |
| O-retinoyl (13-cis)- | 110 | 110 |

|  | Staph. Epi. 3 | Staph. Epi. 6 |
| --- | --- | --- |
| 2'-erythromycin A O-retinoyl (13-cis)-clindamycin | 113 | 113 |
| O-retinoyl (13-cis)-lincomycin | 100 | 100 |
| Controls |  |  |
| Erythromycin A | 13 | 30 |
| Clindamycin | 7 | 8 |
| Lincomycin | 14 | 20 |

The "Staph. Epi. 3" strain is isolated from an acne patient whereas the "Staph. Epi. 6" strain is isolated from a non-acne patient. The isolation of these strains is carried out in accordance with the Williamson-Kligman method, ("A new method for the quantitative investigation of cutaneous bacteria", P. Williamson and A. Kligman, J. I. D., Vol. 45, No. 6, 1965). Decimal dilutions of the retained portions are effected and 0.1 ml of these dilutions is inoculated on a selective medium permitting isolation of staphylococcus.

As can be seen in the first table, the retinoic esters of erythromycin A and lincomycin are more active on the resistant *propionibacterium acnes* strains than the parent antibiotics. Moreover, the oleic ester at the 2'-position of erythromycin A (U.S. Pat. No. 2,862,921) as well as the oleic ester in the 3-position of clindamycin (DOS 2,017,003) taken as comparison esters, are disclosed to be clearly less active on the sensitive strains (P37 E⊕) and resistant strains (P37 E⊖) than the esters of the present invention which thus reinforces the considerable interest in the retinoic esters of erythromycin A and clindamycin. The second table, itself, shows the interest in all these retinoic esters of antibiotics vis-a-vis "cutaneous ecology" since they are much less active on *staphylococcus epidermidis* strains than the parent antibiotics.

The following non-limiting examples illustrate the preparation of the retinoic esters of antibiotics in accordance with the present invention as well as pharmaceutical or cosmetic compositions for the treatment of dermatoses, principally acne.

EXAMPLE 1

Preparation of O-retinoyl (13-cis)-2'-erythromycin A

In a round bottom flask, under an inert atmosphere 5 g (16.6 mmoles) of (13-cis) retinoic acid are dissolved in 35 ml of anhydrous tetrahydrofuran; the reaction mixture is cooled to 0° C. and 3 ml (38 mmoles) of anhydrous pyridine and 1.6 ml (16.6 mmoles) of ethyl chloroformate are added. The solution is stirred for 5 minutes and 2.5 g (30 mmoles) of sodium bicarbonate are added. Then 4.9 g (6.7 mmoles) of erythromycin A previously dissolved in 150 ml of tetrahydrofuran are added. The reaction mixture is then left, with stirring, for 10 hours so as to return to ambient temperature (chromatography on thin layer silica gel; methylene chloride/10% methanol). The solution is poured into 60 ml of water and then extracted with ethylacetate. The organic phase is dried on magnesium sulfate, filtered and then concentrated under a partial vacuum. The resulting crude product is chromatographed on a silica gel column (HPLC) by using, as the eluant, 7 parts ethyl acetate/3 parts hexane thereby isolating 4.4 g (65% yield) of pure O-retinoyl (13-cis)-2'-erythromycin A.

Melting point = 82° C. (hexane/ethylacetate)
$[\alpha]_D^{22} = -17°$ (C = 6 mg/ml dichloromethane)
Microanalysis: $C_{57}H_{93}NO_{14}$; Mass = 1016.4

|  | C | H | N |
| --- | --- | --- | --- |
| Calculated, % | 67.36 | 9.22 | 1.38 |
| Found, % | 67.48 | 9.32 | 1.38 |

° Infrared: Band at 1735 cm¹ (ester)
NMR of $^{13}C$ (CDCl$_3$, ref. internal T.M.S.)
Negative γ effects at the 1'-position (−2.2 ppm) and 3'-position (−2.1 ppm) indicate the position of the ester in the 2'-position. The C"$_{20}$ carbon (20.94 ppm), C"$_{14}$ carbon (117.28 ppm) and C"$_{12}$ carbon (131.9 ppm) of the retinoic chain are in agreement with the 13-cis stereochemistry of the retinoic chain.

EXAMPLE 2

Preparation of O-retinoyl (all trans)-2'-erythromycin A

In a round bottom flask, under an inert atmosphere, 5 g (16.6 mmoles) of (all trans) retinoic acid are dissolved in 35 ml of anhydrous tetrahydrofuran. The reaction mixture is cooled to 0° C. and 3 ml (38 mmoles) of anhydrous pyridine and 1.6 ml (16.6 mmoles) of ethyl chloroformate are added. The solution is stirred for 5 minutes and 2.5 g (30 mmoles) of sodium bicarbonate are added. Then 4.9 g (6.7 mmoles) of erythromycin A previously dissolved in 150 ml of tetrahydrofuran are added. The reaction mixture is then left, with stirring, for 10 hours to let it return to ambient temperature (chromatography on thin layer silica gel: methylene chloride/10% methanol). The solution is poured into 60 ml of water and then extracted with ethyl acetate. The organic phase is dried on magnesium sulfate, filtered and then concentrated under a partial vacuum. The resulting crude product is chromatographed on a silica gel column (HPLC) by using, as the eluant, 7 parts ethylacetate/3 parts hexane thereby isolating 4.1 g (60% yield) of pure O-retinoyl (all trans)-2'-erythromycin A.

Melting point: 76° C. (ethylacetate/hexane)
$[\alpha]_D^{22} = -65°$ (C = 2 mg/ml dichloromethane)
Microanalysis: $C_{57}H_{93}NO_{14} \cdot 4H_2O$; Mass = 1088.5

|  | C | H | N |
| --- | --- | --- | --- |
| Calculated, % | 62.89 | 9.35 | 1.29 |
| Found, % | 62.91 | 8.90 | 1.29 |

NMR of $^{13}C$ (CDCl$_3$, ref. internal T.M.S.)
Negative γ effects in the 1'-position (−2 ppm) and the 3'position (−1.9 ppm) indicate the position of the ester in the 2'-position. The C"$_{20}$ carbon (14.1 ppm), C"$_{14}$ carbon (119.36 ppm) and C"$_{12}$ carbon (135.19 ppm) are in agreement with the all trans stereochemistry of the retinoic chain.

EXAMPLE 3

Preparation of O-retinoyl (all trans)-3-clindamycin

In a round bottom flask, under an inert atmosphere, 5 g (16.6 mmoles) of (all trans) retinoic acid are dissolved in 30 ml of anhydrous tetrahydrofuran. The reaction mixture is cooled to 0° C. 6 ml (76 mmoles) of anhydrous pyridine and 1.6 ml (16.6 mmoles) of ethyl chloroformate are added. The solution is stirred for 5 minutes and 1.25 g (15 mmoles) of sodium bicarbonate are added. Then 2.35 g (5.5 mmoles) of clindamycin previously dissolved in 100 ml of a tetrahydrofuran (8)/pyridine (2) mixture are added. The reaction mixture is then left, with stirring, for 10 hours to return to ambient temperature (chromatography on thin layer silica gel: methylene chloride/5% methanol). The solution is poured into 80 ml of water and then extracted with ethyl acetate. The organic phase is dried on magnesium sulfate, filtered and then concentrated under a partial vacuum. The resulting crude product is chromatographed on a silica gel column (HPLC) by using as the eluant: ethylacetate (5)/hexane (5) thereby isolating 2.15 g (55% yield) of pure O-retinoyl (all trans)-3-clindamycin.

Melting point = 62° C.
$[\alpha]_D^{22} = +50°$ (C = 100 mg/ml dichloromethane)
Microanalysis: $C_{32}H_{59}N_2SO_6Cl.2.5H_2O$; Mass = 752.5

|  | C | H | N |
|---|---|---|---|
| Calculated, % | 60.44 | 8.08 | 3.23 |
| Found, % | 60.66 | 8.57 | 3.72 |

NMR OF $^{13}C$. (CDCL$_3$, ref. internal T.M.S.)

Negative $\gamma$ effects in the 4-position ($-2.8$ ppm) and in the 2-position ($-1.9$ ppm) indicate the position of the ester in the 3-position. The chemical displacements of the $C''_{14}$ carbon (117.84 ppm) and $C''_{20}$ carbon (14.11 ppm) confirm the all trans stereochemistry of the retinoyl chain.

EXAMPLE 4

Preparation of O-retinoyl (13-cis)-3-clindamycin

In a round bottom flask, under an inert atmosphere, 5 g (16.6 mmoles) of (13-cis) retinoic acid are dissolved in 30 ml of anhydrous tetrahydrofuran. The reaction mixture is cooled to 0° C. 6 ml (76 mmoles) of anhydrous pyridine and 1.6 ml (16.6 mmoles of ethyl chloroformate are then added. The solution is stirred for 5 minutes and 1.25 g (15 mmoles) of sodium bicarbonate are added. Then 2.35 g (5.5 mmoles) of clindamycin previously dissolved in 100 ml of a tetrahydrofuran (8)/pyridine (2) mixture are added. The reaction mixture is then left, with stirring, for 10 hours to return to ambient temperature (chromatography on thin layer silica gel; methylene chloride/5% methanol). The solution is poured into 80 ml of water and then extracted with ethyl acetate. The organic phase is dried on magnesium sulfate, filtered and then concentrated under a partial vacuum. The resulting crude product is chromatographed on a silica gel column (HPLC) by using as the eluant: ethylacetate (5)/hexane (5) thereby isolating 2 g (51% yield) of pure O-retinoyl (13-cis)-3-clindamycin.

Melting point = 95° C. (Hexane/ethylacetate)
$[\alpha]_D^{22} = +111°$ (C = 15 mg/ml dichloromethane)
Microanalysis: $C_{38}H_{59}ClN_2SO_6$; Mass = 707.4

|  | C | H |
|---|---|---|
| Calculated, % | 64.52 | 8.41 |
| Found, % | 64.47 | 8.45 |

NMR of the $^{13}C$ (CDCl$_3$, ref. internal T.M.S.)

The position of the ester is indicated by the positive $\beta$ effect in the 3-position ($+1.77$ ppm) and the negative $\gamma$ effects in the 2-position ($-1.4$ ppm) and in the 4-position ($-2.5$ ppm). The 13-cis configuration is confirmed by the $C''_{20}$ carbon (20.93 ppm) and the $C''_{14}$ carbon (115.94 ppm).

EXAMPLE 5

Preparation of O-retinoyl (13-cis)-3-lincomycin

In a round bottom flask, under an inert atmosphere, 5 g (16.6 mmoles) of (13-cis) retinoic acid are dissolved in 30 ml of anhydrous tetrahydrofuran. The reaction mixture is cooled to 0° C., 6 ml (76 mmoles) of anhydrous pyridine and 1.6 ml (16.6 mmoles) of ethyl chloroformate are added. The solution is stirred for 5 minutes and 1.25 g (15 mmoles) of sodium bicarbonate are added. Then 2.2 g (5.4 mmoles) of lincomycin, previously dissolved in 100 ml of a tetrahydrofuran (7)/pyridine (3) mixture, are added. The reaction mixture is then left, with stirring, for 10 hours to return to ambient temperature (chromatography on thin layer silica gel: methylene chloride/10% methanol). The solution is poured into 100 ml of water and then extracted with ethylacetate. The organic phase is dried on magnesium sulfate, filtered and then concentrated under a partial vacuum. The resulting crude product is chromatographed on silica gel (HPLC) by using as the eluant: ethylacetate (8)/hexane (2) thereby isolating 1.85 g (50% yield) of pure O-retinoyl (13-cis)-3-lincomycin:

Melting point = 95° C. (hexane/ethylacetate)
$[\alpha]_D^{22} = +103°$ (C = 7 mg/ml dichloroethane)
Microanalysis: $C_{38}H_{60}N_2SO_7.2.5H_2O$; Mass = 734.5

|  | C | H |
|---|---|---|
| Calculated, % | 62.18 | 9.03 |
| Found, % | 62.33 | 8.64 |

NMR of the $^{13}C$ (CDCl$_3$, ref. internal T.M.S.)

The position of the ester is indicated by the positive $\beta$ effect in the 3-position ($+1.6$ ppm) and the negative $\gamma$ effects in the 2-position ($-2.4$ ppm) and in the 4-position ($-1.9$ ppm). The 13 cis configuration is confirmed by the $C''_{20}$ (20.98 ppm) and the $C''_{14}$ (115.83 ppm).

EXAMPLE 6

Preparation of a mixture of monoesters of O-retinoyl (all trans)-7-lincomycin, O-retinoyl (all trans)-3-lincomycin and O-retinoyl (all trans)-2-lincomycin In a round bottom flask, under an inert atmosphere, 30 g (74 mmoles) of lincomycin are dissolved in 300 ml of anhydrous N,N-dimethylformamide. Then 830 mg (7.4 mmoles) of potassium tert.butylate are added and stirring is continued at ambient temperature for 90 minutes. There is then added a solution of 13 g (37 mmoles) of retinoyl (all trans)-1-imidazole in 150 ml of N,N-dimethylformamide and the resulting medium is stirred at ambient temperature for 12 hours (chromatography on thin layer silica gel: methylenechloride/7.5% methanol). The solution is poured into 500 ml of water and then extracted with ethylacetate. The organic phase is dried on magnesium sulfate, filtered and then concentrated under a partial vacuum. The resulting crude product is chromatographed on a silica gel column (HPLC) using as the eluant: ethylacetate (7)/hexane (3) thereby isolating 39 g (77% yield) of a mixture of (all trans) retinoic monoesters of lincomycin in the 2-,3- and 7-positions.

NMR of the $^{13}C$ (CDCl$_3$, ref. internal T.M.S.)

The negative γ effects in the 8-position (−2.5 ppm) and in the 6-position (−3.8 ppm) indicate the esterification site of a monoester at the 7-position.

The negative γ effects in the 1-position (−4 ppm) indicates the monoester in the 2-position and the negative γ effects in the 2-position (−2 ppm) and in the 4-position (−2.6 ppm) indicate the position of the monoester in the 3-position. The positions of $C_1$ are at 85.06 ppm for the monoester in the 2-position, at 88.45 ppm for the monoester in the 7-position and at 89.67 ppm for the monoester in the 3-position.

The confirguation of the all trans retionic chain is indicated for the $C''_{14}$ at 117.78 pm and for the $C''_{20}$ at 14.08 ppm. A trace of isomerization is noted by the presence of a peak at 115.2 ppm ($C''_{14}$), indicating the 13-cis isomer.

EXAMPLE 7

Preparation of a mixture of monoesters of O-retinoyl (all trans)-2-clindamycin, O-retinoyl (all trans)-3-clindamycin and O-retinoyl (all trans)-4-clindamycin In a round bottom flask, under an inert atmosphere, 20 g (47 mmoles) of clindamycin are dissolved in 250 ml of anhydrous N,N-dimethylformamide. Then 527 mg (4.7 mmoles) of potassium tert.butylate are added to the reaction mixture which is then stirred at ambient temperature for 90 minutes. There is then added a solution of 8.250 g (23.5 mmoles) of retinoyl (all trans)-1 imidazole in 150 ml of anhydrous N,N-dimethylformamide and the resulting reaction medium is stirred at ambient temperature for 12 hours (chromatography on thin layer silica gel: methylene chloride/5% methanol). The solution is poured into 500 ml of water and then extracted with ethylacetate: The organic phase is dried on magnesium sulfate, filtered and then concentrated under a partial vacuum. The resulting crude product is chromatographed on a silica gel column (HPLC) using as the eluant: ethylacetate (5)/hexane (5) thereby isolating 28 g (85% yield) of a mixture of (all trans) retinoic esters of clindamycin in the 2-, 3- and 4-positions.

NMR of the $^{13}C$ (CDCl$_3$, ref. internal T.M.S.)

Negative γ effects in the 1-position (−3 ppm) indicates the position of the ester in the 2-position.

The negative γ effects in the 4-position (−2.8 ppm) and the 2-position (−1.9 ppm) indicate the monoester in the 3-position and the weak negative γ effect in the 3-position indicates the monoester in the 4-position.

The positions of the $C_1$ are at 84.63 ppm for the monoester in the 2-position, at 88.79 ppm for the monoester in the 3-position and at 87.98 ppm for the monoester in the 4-position.

The all trans configuration of the retinoic chain predominates ($C''_{14}$ at 117.5 ppm and $C''_{20}$ at (14.08 ppm) but traces of isomerization are evident, principally in $C''_{20}$ and $C''_{14}$.

EXAMPLE 8

Preparation of O-retinoyl (all trans)-9-josamycin

In a round bottom flask, under an inert atmosphere, 5 g (16.6 mmoles) of all trans retinoic acid are dissolved in 35 ml of tetrahydrofuran. The reaction mixture is cooled to 0° C. and 2.5 ml of anhydrous triethylamine and 1.6 ml (16.6 mmoles) of ethyl chloroformate are added. The solution is stirred for 5 minutes and 20 ml of anhydrous pyridine are added. Then 5.8 g (7 mmoles) of josamycin, previously dissolved in 150 ml of tetrahydrofuran are added.

The reaction mixture is then left, with stirring, for 10 hours to return to ambient temperature (chromatography on thin layer silica gel: methylene chloride (90)/methanol (10)). The solution is poured into 60 ml of water and then extracted with ethyl acetate. The organic phase is dried on magnesium sulfate, filtered and then concentrated under a partial vacuum. The resulting crude product is chromatographed on silica gel (HPLC) by using as the eluant: ethylacetate (7)/hexane (3) thereby isolating 4.7 g (60% yield) of O-retinoyl (all trans)-9-josamycin and a trace of its 13-cis isomer.

Melting point = 110° C. (hexane/ethyl acetate)

Microanalysis: $C_{62}H_{95}NO_{16}.1.5H_2O$ Mass = 1137.5

|              | C     | H    | N    |
|--------------|-------|------|------|
| Calculated, %| 65.46 | 8.68 | 1.23 |
| Found, %     | 65.26 | 8.55 | 1.19 |

I.R: band at 1735 cm$^{-1}$ (ester)

NMR of $^{13}C$ (CDCl$_3$; ref. internal T.M.S.)

Negative γ effects at the 8-position (−2.2 ppm) and 10-position (−1.3 ppm) indicate the position of the ester in the 9-position.

EXAMPLE 9

Preparation of O-retinoyl (all trans)-2'-josamycin

In a round bottom flask, under an inert atmosphere, 5 g (16.6 mmoles) of all trans retinoic acid are dissolved in 35 ml of tetrahydrofuran. The reaction mixture is cooled to 0° C. and 3 ml (38 mmoles) of anhydrous pyridine and 1.6 (16.6 mmoles) of ethyl chloroformate are added. The solution is stirred for 5 minutes and 25 ml of anhydrous pyridine are added. Then 5.8 g (7 mmoles) of josamycin, previously dissolved in 150 ml of tetrahydrofuran are added.

The reaction mixture is then left, with stirring, for 10 hours to return to ambient temperature (chromatography on thin layer silica gel: methylene chloride/7.5% methanol). The solution is poured into 100 ml of water and then extracted with ethyl acetate. The organic phase is dried on magnesium sulfate, filtered and then concentrated under a partial vacuum. The resulting crude product is chromatographed on silica gel (HPLC) by using as the eluant: ethyl acetate (7)/hexane (3) thereby isolating 1.5 g (20% yield) of O-retinoyl (all trans)-2'-josamycin and a trace of its 13-cis isomer.

Melting point = 130° C. (hexane/ethyl acetate)

Microanalysis: $C_{62}H_{95}NO_{16}.1.5H_2O$; Mass = 1137.5

|              | C     | H    | N    |
|--------------|-------|------|------|
| Calculated, %| 65.46 | 8.68 | 1.23 |
| Found, %     | 65.76 | 8.21 | 1.22 |

NMR of $^{13}C$ (CDCl$_3$; ref. internal T.M.S.)

Negative γ effects at the 1'-position (−2.9 ppm) and 3'-position (−1.62 ppm) indicate the position of the ester in the 2'-position.

EXAMPLE 10

Preparation of a mixture of O-retinoyl (all trans)-2'-and O-retinoyl (all trans)-4'' oleandomycin In a round bottom flask, under an inert atmosphere, 5 g (16.6 mmoles) of all trans retinoic acid are dissolved in 35 ml of tetrahydrofuran. The reaction mixture is cooled to 0° C. and 2.4 ml (16.7 mmoles) of triethylamine and 1.6 ml (16.6 mmoles) of ethyl chloroformate are added.

The solution is stirred for 5 minutes and 25 ml of anhydrous pyridine are added. Then 4.1 g (6 mmoles) of oleandomycin, previously dissolved in 200 ml of tetrahydrofuran are added.

The reaction mixture is then left, with stirring, for 10 hours to return to ambient temperature (chromatography on thin layer silica gel: methylene chloride (90)/methanol (10)). The solution is poured into 60 ml of water and then extracted with ethyl acetate. The organic phase is dried on magnesium sulfate, filtered and then concentrated under a partial vacuum. The resulting crude product is chromatographed on silica gel (HPLC) by using as the eluant: ethyl acetate (7)/hexane (3) thereby isolating 3.2 (55% yield) of a mixture O-retinoyl (all trans)-4''-oleandomycin and O-retinoyl (all trans)-2'-oleandomycin (The former being in larger amount than the latter).

Microanalysis: $C_{55}H_{87}NO_{13} \cdot 1.5H_2O$; Mass=997

|  | C | H | N |
|---|---|---|---|
| Calculated, % | 66.24 | 9.09 | 1.40 |
| Found, % | 66.23 | 8.96 | 1.50 |

NMR of $^{13}C$ (CDCl$_3$; ref. internal T.M.S.)

Negative $\gamma$ effects at the 3'-position (−2.5 ppm) and 5''-position (−1.5 ppm) indicate the position of the ester in the 4''-position (larger amount)

EXAMPLE 11

Preparation of O-retinoyl (13-cis)-2'-roxythromycin

In a round bottom flask, under an inert atmosphere, 5 g (16.6 mmoles) of 13-cis retinoic acid are dissolved in 35 ml of tetrahydrofuran. The reaction mixture is cooled to 0° C. and 2.5 ml of anhydrous triethylamine and 1.6 ml (16.6 mmoles) of ethyl chloroformate are added.

The solution is stirred for 5 minutes and 25 ml of anhydrous pyridine are added. Then 5 g (6 mmoles) of roxithromycin, previously dissolved in 150 ml of tetrahydrofuran are added.

The reaction mixture is then left, with stirring, for 10 hours to return to ambient temperature (chromatography on thin layer silica gel: methylene chloride (90)/methanol (10)). The solution is poured into 120 ml of water and then extracted with ethyl acetate. The organic phase is dried on magnesium sulfate, filtered and then concentrated under a partial vacuum. The resulting crude product is chromatographed on silica gel (HPLC) by using as the eluant: ethyl acetate (7)/hexane (3) thereby isolating 4 g (60% yield) of O-retinoyl (13-cis)-2'-roxythromycin and a trace of its all trans isomer.

Melting point=117° C. (hexane/ethyl acetate)
Microanalysis: $C_{61}H_{102}NO_{16} \cdot 3H_2O$; Mass=1173,6

|  | C | H | N |
|---|---|---|---|
| Calculated, % | 62.43 | 9.28 | 2.39 |
| Found, % | 62.39 | 8.65 | 2.21 |

NMR of $^{13}C$ (CDCl$_3$; ref. internal T.M.S.)

Negative $\gamma$ effects at the 1'-position and 3'-position indicate the position of the ester in the 2'-position.

PHARMACEUTICAL AND COSMETIC COMPOSITIONS

A—Gels For The Topical Treatment of Acne

Example 1

| Hydroxypropyl cellulose | 1 g |
|---|---|
| Butylhydroxytoluene | 0.05 g |
| O-retinoyl (13-cis)-3-lincomycin | 0.5 g |
| Isopropanol, sufficient amount for | 100 g |

In this Example, the active compound can be replaced by the same amount of O-retinoyl (all trans)-9-josamycin.

Example 2

| Hydroxypropyl cellulose | 1.5 g |
|---|---|
| Butylhydroxytoluene | 0.05 g |
| O-retinoyl (all trans)-3-clindamycin | 0.3 g |
| Isopropanol, sufficient amount for | 100 g |

B-Lotions For the Topical Treatment of Acne

Example 3

| Butylhydroxytoluene | 0.05 g |
|---|---|
| O-retinoyl (all trans)-2'-erythromycin A | 1 g |
| Triglycerides of $C_8$–$C_{12}$ fatty acids, sufficient amount for | 100 g |

In this example, the active compound can be replaced by the same amount of O-retinoyl (13-cis)-2'-erythromycin A.

Example 4

| Butylhydroxytoluene | 0.05 g |
|---|---|
| O-retinoyl (13-cis)-3-clindamycin | 0.7 g |
| Dimethylether of polytetrahydrofuran, viscosity 22 centipoises, having the formula: $CH_3O+(CH_2)_2-CH_2-CH_2-O]_{\overline{n}}CH_3$ wherein n = 5, sufficient amount for | 100 g |

Example 5

| Butylhydroxytoluene | 0.05 g |
|---|---|
| O-retinoyl (all trans)-9-josamycin | 1 g |
| Triglycerides of $C_8$–$C_{12}$ fatty acids, sufficient amount for | 100 g |

C—Stick for the Topical Treatment of Acne

Example 6

White petrolatum: 52 g.
Petrolatum oil: 15 g.
Raffinated paraffin: 32 g.
O-retinoyl (all trans)-2'-erythromycin A: 1 g.

In this example, the active compound can be replaced by the same amount of O-retinoyl (all trans)-9-josamycin.

D—Suppository (Composition For 1 Unit)

Example 7

O-retinoyl (all trans)-2'-erythromycin A: 0.05 g.
Triglycerides of $C_8-C_{12}$ fatty acids 0.25 g.
Semi-synthetic glycerides: 2 g.

E—500 mg Capsules

The walls of the capsules are made of glycerine, sorbitol and gelatin.

Example 8

Capsule containing 50 mg of active compound
O-retinoyl (13-cis)-2'-erythromycin A: 50 mg.
Liquid petrolatum oil: 200 mg.
Thick petrolatum oil: 250 mg.

Example 9

Capsule containing 10 mg of active compound
O-retinoyl (13-cis)-2'-erythromycin A: 10 mg.
Butylhydroxyaminose: 0.05 mg.
Butylhydroxytoluene: 0.05 mg.
Glycerol tribehenate: 100 mg.
Triglycerides of $C_8-C_{12}$ fatty acids, sufficient amount for: 500 mg.

F—Gelules

The walls of the gelules are made of gelatin and titanium dioxide.

Example 10

O-retinoyl (all trans)-2'-erythromycin A: 20 mg.
Colloidal silica: 2 mg.
Magnesium stearate: 2 mg.
Cornstarch: 76 mg.
Lactose, sufficient amount for: 250 mg.

What is claimed is:

1. An all trans or 13-cis retinoic ester of a macrolide or lincosamide having the formula

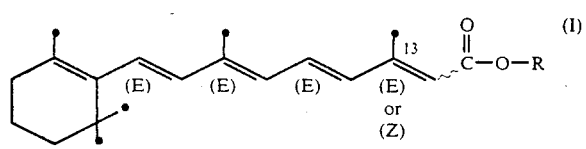

wherein
R represents a macrolide selected from the group consisting of:
erythromycin A substituted in the 2' position,
roxithromycin substituted in the 2' position,
oleandomycin substituted in the 2' position,
oleandomycin substituted in the 4" position,
oleandomycin substituted in the 2' and 4" positions,
josamycin substituted in the 9 position,
josamycin substituted in the 2' position,
josamycin substituted in the 9 and 2' positions,
spiramycin (I) substituted in the 2' position,
spiramycin (I) substituted in the 4" position,
spiramycin (I) substituted in the 2' and 4" positions,
spiramycin (II) substituted in the 2' position,
spiramycin (II) substituted in the 4" position,
spiramycin (II) substituted in the 2' and 4" positions,
spriamycin (III) substituted in the 2' position,
spiramycin (III) substituted in the 4" position,
spiramycin (III) substituted in the 2' and 4" positions,
or R represents a lincosamide selected from the group consisting of
lincomycin substituted in the 3 position,
clindamycin substituted in the 3 position,
lincomycin substituted in the 2, 4 and 7 positions and
clindamycin substituted in the 2 and 4 positions.

2. The ester of claim 1 selected from the group consisting of:
O-retinoyl (all trans)-2'-erythromycin A,
O-retinoyl (13-cis)-2'-erythromycin A,
O-retinoyl (13-cis)-2'-roxithromycin,
O-retinoyl (all trans)-2'-oleandomycin,
O-retinoyl (all trans)-9-josamycin,
O-retinoyl (all trans)-2-josamycin,
O-retinoyl (13-cis)-2'-spiramycin (I),
O-retinoyl (13-cis)-2'-spiramycin (II),
O-retinoyl (13-cis)-2'-spiramycin (III),
O-retinoyl (all trans)-3-spiramycin (I),
O-retinoyl (all trans)-3-spiramycin (II),
O-retinoyl (all trans)-3-spiramycin (III),
O-retinoyl (13-cis)-9-josamycin,
O-retinoyl (13-cis)-3-lincomycin,
O-retinoyl (13-cis)-3-clindamycin,
O-retinoyl (all trans)-7-lincomycin,
O-retinoyl (all trans)-3-lincomycin,
O-retinoyl (all trans)-2-lincomycin,
O-retinoyl (all trans)-2-clindamycin,
O-retinoyl (all trans)-3-clindamycin,
O-retinoyl (all trans)-4-clindamycin, and mixtures thereof.

3. A composition for the treatment of dermatosis comprising in an anhydrous vehicle an amount effective to treat said dermatosis of an all trans or 13-cis retinoic ester of a macrolide or lincosamide of claim 1, a salt thereof or a mixture thereof.

4. The composition of claim 3 wherein said ester is present in an amount ranging from 0.001 to 10 percent by weight based on the total weight of said composition.

5. The composition of claim 3 wherein said ester is present in an amount ranging from 0.01 to 1 percent by weight based on the total weight of said composition.

6. The composition of claim 3 wherein said anhydrous vehicle is selected from the group consisting of acetone, isopropyl alcohol, triglycerides of a fatty acid, $C_1-C_4$ alkyl ester of a short chain acid, a polytetrahydrofuran ether, a volatile silicone and a mixture thereof.

7. The composition of claim 3 which also contains a thickening agent present in an amount ranging from 0.5 to 20 percent by weight based on the total weight of said composition.

8. The composition of claim 7 wherein said thickening agent is cellulose or a derivative thereof.

9. The composition of claim 3 which also contains an antioxidant, a preservative, a perfume, a dye or an anti-acne agent other than said ester.

10. A method for treating dermatosis comprising administering to a person affected by said dermatosis an effective amount of the composition of claim 3.

11. The method of claim 10 wherein said composition is administered orally at a rate of about 0.1 mg–5 mg/Kg of body weight/day.

12. The method of claim 10 wherein said composition is administered topically to the area of the skin of a person affected by said dermatosis at a rate of 2–3 times each day for a period of time ranging from 6 to 30 weeks.

* * * * *

UNITED STATES PATENT AND TRADEMARK OFFICE
CERTIFICATE OF CORRECTION

PATENT NO. : 5,045,533

DATED : September 3, 1991

INVENTOR(S) : Philippe et al

Page 1 of 2

It is certified that error appears in the above-identified patent and that said Letters Patent is hereby corrected as shown below:

Col. 5, lines 10 to 35 should read:

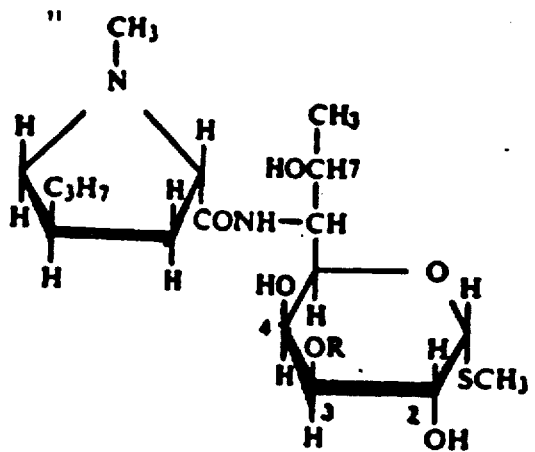

UNITED STATES PATENT AND TRADEMARK OFFICE
CERTIFICATE OF CORRECTION

PATENT NO. : 5,045,533

DATED : September 3, 1991

INVENTOR(S) : Philippe et al

It is certified that error appears in the above-identified patent and that said Letters Patent is hereby corrected as shown below:

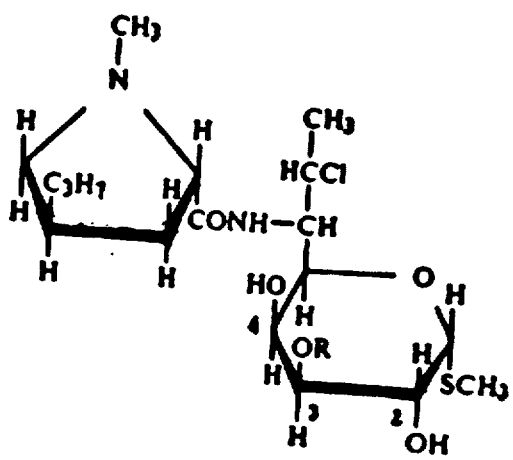

VII

Signed and Sealed this

Twenty-seventh Day of April, 1993

*Attest:*

MICHAEL K. KIRK

*Attesting Officer*   *Acting Commissioner of Patents and Trademarks*